(12) United States Patent
Scherer et al.

(10) Patent No.: US 10,175,235 B2
(45) Date of Patent: Jan. 8, 2019

(54) OPTICAL RESONATOR DIAGNOSTIC DEVICE AND METHODS OF USE

(71) Applicant: CALIFORNIA INSTITUTE OF TECHNOLOGY, Pasadena, CA (US)

(72) Inventors: Axel Scherer, Barnard, VT (US); Samuel Njoroge, Cincinnati, OH (US); Jingqing Huang, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 288 days.

(21) Appl. No.: 15/157,346

(22) Filed: May 17, 2016

(65) Prior Publication Data

US 2016/0258942 A1 Sep. 8, 2016

Related U.S. Application Data

(62) Division of application No. 13/684,020, filed on Nov. 21, 2012, now Pat. No. 9,435,803.

(Continued)

(51) Int. Cl.

| | |
|---|---|
| *G01N 33/543* | (2006.01) |
| *G01N 33/566* | (2006.01) |
| *A61B 5/1459* | (2006.01) |
| *G01N 21/41* | (2006.01) |
| *G01N 33/552* | (2006.01) |
| *A61B 5/1491* | (2006.01) |

(52) U.S. Cl.
CPC ......... *G01N 33/566* (2013.01); *A61B 5/1459* (2013.01); *G01N 21/41* (2013.01); *G01N 33/54373* (2013.01); *G01N 33/552* (2013.01); *A61B 5/1491* (2013.01); *A61B 2562/0233* (2013.01); *A61B 2562/043* (2013.01); *G01N 2201/068* (2013.01); *G01N 2201/08* (2013.01)

(58) Field of Classification Search
None
See application file for complete search history.

(56) References Cited

U.S. PATENT DOCUMENTS

| | | | |
|---|---|---|---|
| 5,663,790 A | * | 9/1997 | Ekstrom ................ G01N 21/41 204/452 |
| 9,435,803 B2 | | 9/2016 | Scherer et al. |

(Continued)

OTHER PUBLICATIONS

International Preliminary Report on Patentability issued for International Patent Application No. PCT/US2012/066405, filed Nov. 21, 2012 on behalf of California Institute of Technology, dated Jun. 5, 2014. 8 pages.

(Continued)

*Primary Examiner* — Rebecca L Martinez
(74) *Attorney, Agent, or Firm* — Steinfl + Bruno LLP

(57) ABSTRACT

An implantable diagnostic device in accordance with the present disclosure provides various benefits such as a compact size thereby allowing implanting of the device inside animate objects; low cost due to incorporation of inexpensive detection circuitry and the use of conventional IC fabrication techniques; re-usability by heating thereby allowing multiple diagnostic tests to be performed without discarding the device; and a configuration that allows performing of simultaneous and/or sequential diagnostic tests for detecting one or more similar or dissimilar target molecules concurrently or at different times.

18 Claims, 7 Drawing Sheets

Related U.S. Application Data

(60) Provisional application No. 61/562,308, filed on Nov. 21, 2011.

(56) References Cited

U.S. PATENT DOCUMENTS

| | | | | |
|---|---|---|---|---|
| 2004/0023396 A1* | 2/2004 | Boyd | ............... | G01N 21/7746 385/12 |
| 2007/0196043 A1* | 8/2007 | Peled | ............... | G01N 21/774 385/12 |
| 2007/0252981 A1* | 11/2007 | Spillane | ............... | G01J 3/44 356/301 |
| 2009/0314763 A1* | 12/2009 | Chu | ............... | G02B 6/12007 219/476 |
| 2013/0130254 A1 | 5/2013 | Scherer et al. | | |

OTHER PUBLICATIONS

Written Opinion issued for International Patent Application No. PCT/US2012/066405, filed Nov. 21, 2012 on behalf of California Institute of Technology, dated Mar. 4, 2013. 6 pages.

\* cited by examiner

OPTICAL RESONATOR DIAGNOSTIC DEVICE AND METHODS OF USE

CROSS REFERENCE TO RELATED APPLICATIONS

The present application is a divisional of U.S. patent application Ser. No. 13/684,020 filed Nov. 21, 2012, which, in turn claims priority to U.S. Provisional Application 61/562,308 filed on Nov. 21, 2011, entitled "Optically Interrogated Microcalorimeter," each of which is incorporated herein by reference.

FIELD

The present teachings relate to diagnostic devices that may be used for detecting molecules in bio-molecular bindings. More in particular, the present disclosure relates to an optical resonator diagnostic device and methods of use.

BACKGROUND

Existing techniques for bio-molecular detection typically require undesirably expensive, complicated and bulky equipment. One example of a technique using such equipment is described in reference [1]. It is desirable to address such handicaps in prior art diagnostic techniques and equipment.

SUMMARY

According to a first aspect of the present disclosure, a diagnostic device fabricated in silicon includes: an optical resonator, an optical waveguide, and a detector. The optical resonator has a capture agent located at a binding site; the optical waveguide is configured for propagating a laser beam, and for coupling a first portion of the propagated laser beam into the optical resonator. The detector is configured for detecting: a) a first resonant wavelength generated by the first optical resonator when no binding reaction is present at the binding site, and b) a second resonant wavelength generated by the first optical resonator upon undergoing a change in refractive index when a binding reaction is present at the first binding site.

According to a second aspect of the present disclosure, a diagnostic device fabricated in silicon includes: an array of optical resonators, an optical waveguide, and an array of detectors. The optical resonator has an immunoassay site; the optical waveguide is configured for coupling coherent light into each optical resonator in the array of optical resonators; and each detector in the array of detectors, which is optically coupled to the array of optical resonators, is configured to detect: a) a first resonant wavelength generated by a corresponding optical resonator, and b) a second resonant wavelength generated by the corresponding optical resonator upon undergoing a change in refractive index by binding of at least one molecule to the immunoassay site.

According to a third aspect of the present disclosure, a method of using a diagnostic device includes: propagating a laser beam through an optical waveguide of the diagnostic device; coupling at least a portion of the laser beam into a first optical resonator located in the diagnostic device, the first optical resonator comprising an immunoassay site; detecting a first current in a first optical detector coupled to the first optical resonator, the first current indicative of a first resonant frequency generated by the first optical resonator in response to the coupling of the at least a portion of the laser beam into the first optical resonator; and detecting a second current in the first optical detector, the second current indicative of an immunoassay binding occurring at the immunoassay site, the immunoassay binding characterized by a change in refractive index in the first optical resonator and a corresponding change in the first resonant frequency.

Further aspects of the disclosure are shown in the specification, drawings and claims of the present application.

BRIEF DESCRIPTION OF THE DRAWINGS

The accompanying drawings, which are incorporated into and constitute a part of this specification, illustrate one or more embodiments of the present disclosure and, together with the description of a few example embodiments, serve to explain the principles and implementations of the disclosure. The components in the drawings are not necessarily drawn to scale. Instead, emphasis is placed upon clearly illustrating various principles. Moreover, in the drawings, like reference numerals designate corresponding parts throughout the several views.

DETAILED DESCRIPTION

Figure 1:
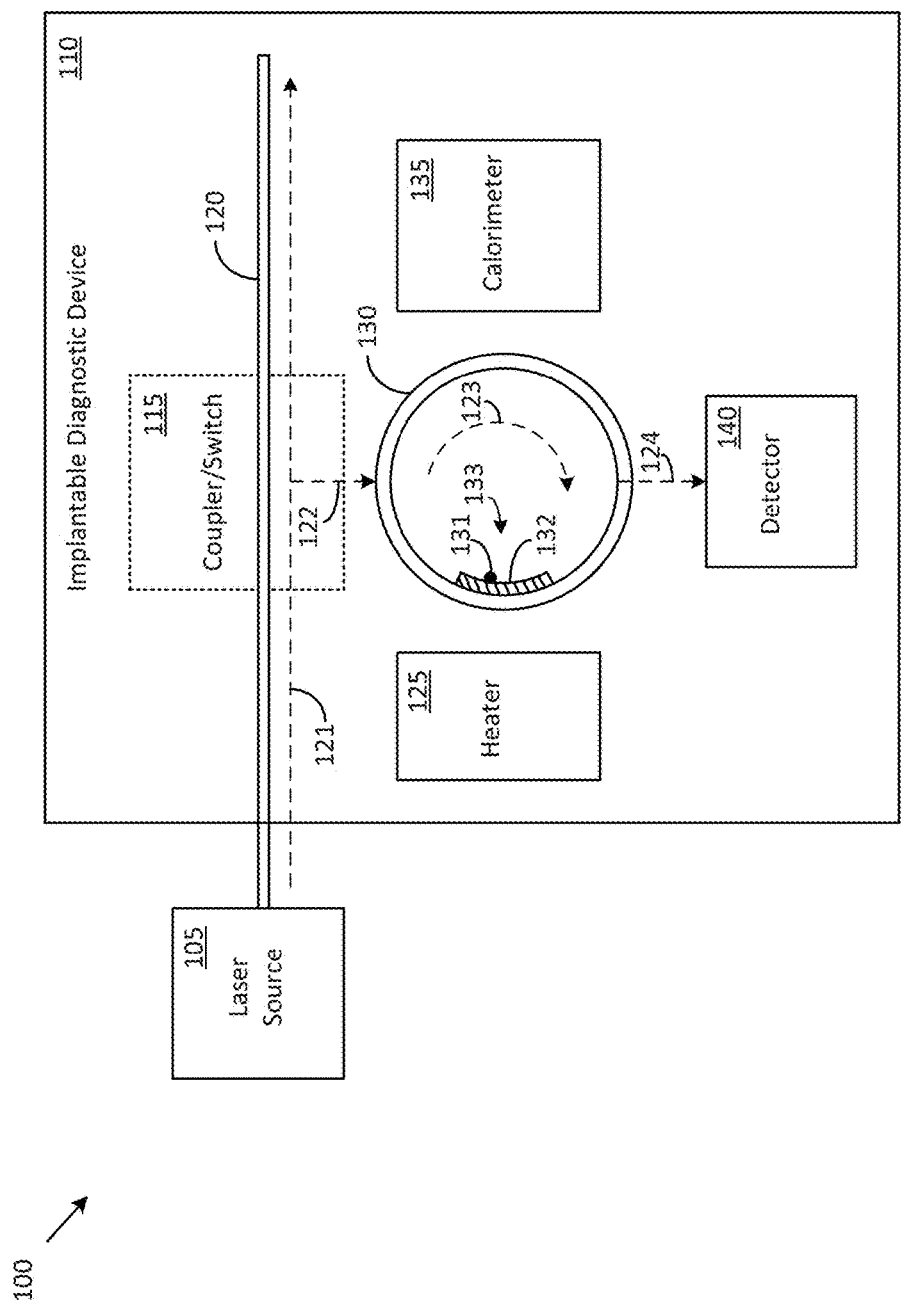
FIG. 1 shows a diagnostic system that includes an implantable diagnostic device in accordance with a first embodiment of the present disclosure.

Throughout this description, embodiments and variations are described for the purpose of illustrating uses and implementations of the inventive concept. The illustrative description should be understood as presenting examples of the inventive concept, rather than as limiting the scope of the concept as disclosed herein. Furthermore, the use of certain words and/or phrases should be understood in the context of the description and it should be understood that in some instances alternative words or phrases may be used to refer to substantially similar actions or elements. As one example of such usage, it should be understood that phrases such as "a binding site" or "an immunoassay site" generally refer to a location in an optical isolator wherein a binding agent (referred to herein variously as "a capture agent" or "an aptamer") is placed in order to provide a binding mechanism for binding an object of interest (referred to herein variously as "molecule", "a foreign molecule", "a target molecule", or "a protein"). The use of such words will be understood in a broad sense by persons of ordinary skill in the art and should not be construed as limiting or exclusionary in nature. It will be further understood that the word "implantable" is intended to indicate that the diagnostic device can be implanted inside certain objects. However, nothing precludes the implantable diagnostic device being configured and/or used in various applications outside an object. For example, the implantable diagnostic device in accordance with the disclosure can be used for carrying out tests (such as an assay test using a hand-held apparatus) conducted in a laboratory for purposes of analyzing a fluid or a liquid.

The various embodiments described herein are generally directed at a diagnostic system that includes a diagnostic device providing several advantages. A few examples of such advantages include: a compact size that allows implanting of the device inside animate objects; integrated/compact packaging that includes a low-cost detector device; manufacturability using existing silicon processes; re-usability as a result of a controllable regeneration mechanism that allows for performing multiple diagnostic tests without removal from an implant location (a human body, for example); and a configuration that allows performing of simultaneous and/or sequential diagnostic tests for detecting one or more similar or dissimilar target molecules concurrently or at different times.

Particularly, a diagnostic device in accordance with the present disclosure is an implantable diagnostic device fabricated in silicon that includes one or more lithographically defined optical sensors together with associated one or more low cost detectors and heaters. The implantable diagnostic device can be inserted into the blood stream of an animal or a human being, for example, and operated to perform label-free diagnostic tests without having to remove the diagnostic device from the animal or human being for purposes of obtaining results, or for purposes of regenerating the diagnostic device for more than one test. These tests may be carried out with significantly more sensitivity than conventional immunoassay and ELISA methods. These, and other, features of the implantable diagnostic device will be described below in further detail using the various figures.

Attention is first drawn to FIG. 1, which shows a diagnostic system 100 that includes an implantable diagnostic device 110 in accordance with a first embodiment of the present disclosure. Implantable diagnostic device 110 includes an optical waveguide 120 for propagating a laser beam that is injected into implantable diagnostic device 110 by a coherent light source such as laser source 105. While implantable diagnostic device 110 can be implanted into a blood stream of an animal or human being, laser source 105 is typically located outside the animal or human being. However, in certain embodiments, laser source 105 may be configured for insertion into the animal or human being, either as an integrated package that contains both laser source 105 as well as implantable diagnostic device 110; or as a separate first package containing laser source 105, with the first package coupled to a second package containing implantable diagnostic device 110.

A portion of the coherent light beam injected by laser source 105 into optical waveguide 120 is diverted from the main light beam path 121 as an auxiliary light beam that is coupled into optical resonator 130 via an auxiliary light beam path 122. The diversion may be carried out in a variety of ways. For example, in a first implementation, coupler/switch 115 is a coupler that taps into the main light beam path 121 to access a portion of the light beam. In a second implementation, coupler/switch 115 is an optical switch that diverts all or a portion of the coherent light beam from main light beam path 121 into auxiliary light beam path 122. Optical couplers and optical switches are known in the art, and will not be elaborated upon herein so as to avoid detracting from the primary focus of the present disclosure.

The coherent light beam propagated via auxiliary light beam path 122 is coupled into optical resonator 130 where the beam is circulated (as indicated by arrow 123) in order to generate a resonant wavelength. Optical resonator 130 is shown in FIG. 1 as a circular resonator, but it should be understood that optical resonator 130 may be implemented in a variety of ways, including resonators having a non-circular structure.

Auxiliary light beam path 122 that is coupled into optical resonator 130 is directed into an optical resonant cavity, for example, a "whispering gallery" structure (not shown) that is known in the prior art. In general, when broad spectrum light is introduced into an optical resonant cavity, only specific wavelengths, referred to herein as resonant wavelengths, are reinforced inside the optical resonant cavity as a result of constructive interference. The resonant wavelengths are determined on the basis of a length of an optical path in a waveguide structure of the optical resonant cavity (for example, a length of the propagation path in a whispering gallery). More specifically, resonant wavelengths are determined on the basis of optical path lengths configured in accordance to integer multiples of the respective half-wavelengths of the resonant wavelengths.

In the present disclosure, optical resonator 130 provides for at least two resonant wavelengths. The first resonant wavelength is determined by a first optical characteristic of optical resonator 130, particularly, in terms of a first optical signal path length, an absorption parameter, and/or a first refractive index of the optical signal path length. One or more of these parameters are defined in part by a binding site 133. Binding site 133, which is located upon an internal surface of the optical resonant cavity of optical resonator 130, contains a capture agent 132 (an aptamer, for example). Capture agent 132 is selectively located on the internal surface in a manner that facilitates a foreign molecule 131 (alternatively referred to herein as a "target" molecule) from binding to capture agent 132. The foreign molecule 131 may be a target molecule flowing in a blood stream of a human being (wherein the target molecule is of specific interest in a diagnostic test). Further details pertaining to this topic will be provided below.

The first resonant wavelength is defined when no foreign molecule 131 is bound to capture agent 132 present at binding site 133.

In contrast, a second resonant wavelength is defined when a foreign molecule 131 is present at binding site 133. The presence of the foreign molecule 131 at binding site 133 modifies the refractive index of the first optical signal path, thereby changing the first resonant wavelength to the second resonant wavelength.

The shift from the first resonant wavelength to the second resonant wavelength provides an indication that foreign molecule 131 is present at binding site 133. In other words, implantable diagnostic device 110 uses the resonant wavelength shift for detecting an occurrence of a bio-molecular binding. Such a wavelength-oriented detection process not only provides high detection sensitivity in implantable diagnostic device 110 but also provides additional advantages. For example, implantable diagnostic device 110 in accordance with the disclosure can be used for re-usable, label-free bio-molecular detection in real time or near-real time (at millisecond intervals, for example).

Implantable diagnostic device 110 further includes a detector 140, which, in contrast to expensive, complex and bulky prior art detection devices, can be fabricated on silicon inside the same package containing optical resonator 130, thereby providing various advantages such as compact size, low cost, and high detection sensitivity.

Detector 140 is basically an optical-to-electrical converter (O/E converter) that accepts light provided out of optical resonator 130, and generates an electrical signal, say in the form of a detector current. More specifically, detector 140 generates a first electrical signal (say, a first detector current) in response to light provided by optical resonator 130 at the first resonant wavelength, and generates a second electrical signal (say, a second detector current) in response to light provided by optical resonator 130 at the second resonant wavelength.

In addition to incorporating detector 140, in some implementations, implantable diagnostic device 110 incorporates a heater 125 and a calorimeter 135. Heater 125 is used to heat optical resonator 130, and more particularly in some cases, at least a portion of optical resonator 130 that houses binding site 133. Heating can be carried out for a variety of reasons. For example, heating can be carried out to detect and record a thermal response of foreign molecule 131 when bound to capture agent 132 at binding site 133, and/or to release foreign molecule 131 from capture agent 132 in order to prepare binding site 133 to accommodate another foreign molecule 131 (of the same type, or a different type) as part of a subsequent diagnostic test.

When used for recording a thermal response, detector 140 provides data via various electrical signals (for example, detector currents) that correspond to various resonant wavelengths. The data may be mapped as a graph of a slope of resonance shift versus time. Since the slope increases with say, an antigen concentration, a standard curve can be compiled to calibrate the antigen concentration over time. The standard curve may then be used to identify unknown concentration values based on one or more electrical signals generated in detector 140.

As pointed out above, detector 140 provides various advantages for example, in terms of lower cost in comparison to prior art externally located measurement equipment, and in terms of increased efficiency and performance as a result of integration into an implantable package in proximity to optical resonator 130.

Calorimeter 135 can be used to measure the temperature of optical resonator 130, or more particularly in some cases, of binding site 133, when detector 140 is used to generate the various signals thereby facilitating mapping of the graph described above. Integrating calorimeter 135 inside implantable diagnostic device 110 provides various advantages, for example, in terms of lower cost in comparison to prior art externally located calorimeters, and in terms of increased efficiency and performance as a result of being located in proximity to optical resonator 130. However, it will be understood that in some implementations, calorimeter 135 may not be included in its entirety inside implantable diagnostic device 110 but may instead be located external to implantable diagnostic device 110. For example, a temperature sensor may be located inside implantable diagnostic device 110 and a read-out unit may be located external to implantable diagnostic device 110. (It may also be pertinent to point out that FIG. 1 does not show connectivity and access elements, such as metal tracks, wires, pins, and connectors, so as to avoid obfuscating the main focus of the disclosure).

Figure 2:
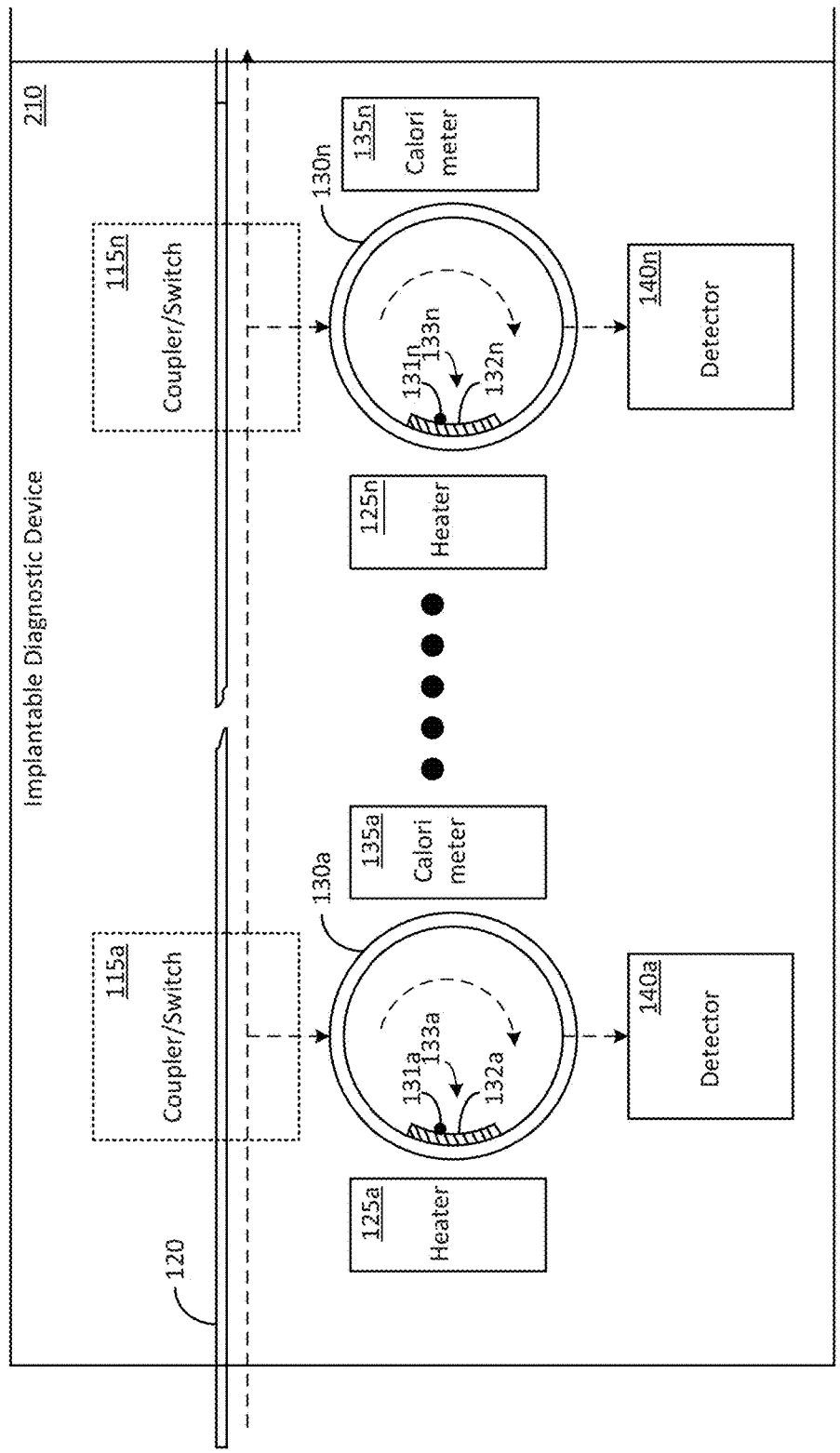
FIG. 2 shows an implantable diagnostic device in accordance with a second embodiment of the present disclosure.

Attention is now drawn to FIG. 2, which shows an implantable diagnostic device 210 in accordance with a second embodiment of the present disclosure. In contrast to implantable diagnostic device 110 of FIG. 1, which incorporates a single optical resonator 130, implantable diagnostic device 210 incorporates an array of optical resonators.

In a first example implementation, each of the optical resonators in the array of optical resonators is substantially similar to optical resonator 130 of FIG. 1. The other elements (detector, heater, and calorimeter) are also substantially similar between the two embodiments. While only two optical resonator circuits are shown, it will be understood that the array of optical resonators can include "N" (N>2) number of optical resonators as indicated by the "a" through "n" suffixes in the various labels.

In a second example implementation, at least one optical resonator in the array of optical resonators does not include a binding site having a capture agent for capturing a foreign molecule. If a single optical resonator is configured in this manner, this single optical resonator can be used as a "reference" optical resonator for various measurement purposes.

For example, in one application, a "reference" current generated in a "reference" detector (associated with a reference optical resonator having no binding site) is used for analyzing one or more currents detected in one or more other optical resonators wherein binding sites are provided.

In other words, the reference current, which corresponds to a first resonant wavelength in the reference optical resonator (due to the lack of a binding site), can be compared to a first current generated in a first optical resonator when no binding reaction is present (i.e. corresponding to a first resonant wavelength). This comparison can be carried out for example, as part of a calibration procedure. Subsequently, when a binding reaction occurs in the first optical resonator, a second current is generated in the first optical resonator (as described above). The difference value between the first and second currents in the first optical resonator can be compared to a difference value between the reference current (in the reference optical resonator) and the second current in the first optical resonator. As can be understood, if the first optical resonator was well calibrated, the two results will be identical. Other such comparisons between the reference current and other currents generated in other optical resonators can be used for various calibration and/or measurement purposes.

Figure 3:
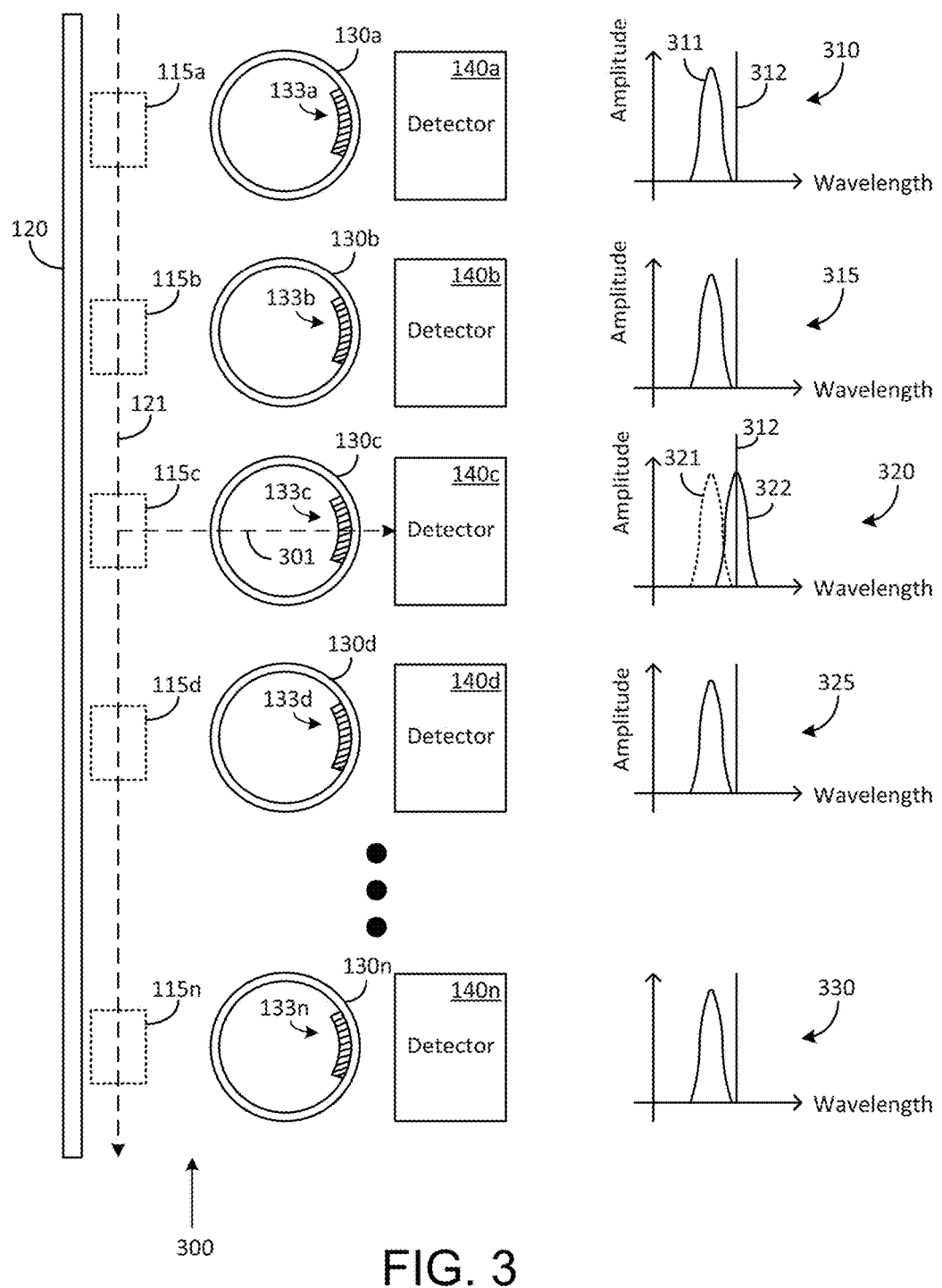
FIG. 3 shows some wavelength-related operational aspects pertaining to the implantable device shown in FIG. 2.

FIG. 3 shows some wavelength-related operational aspects pertaining to implantable diagnostic device 210 shown in FIG. 2. The array of optical resonators 300 can be used for performing various types of diagnostic tests such as individual diagnostic tests, concurrent tests, sequential tests etc., which will be described below in further detail.

In a first example test procedure, each of coupler/switch 115$a$-$n$ is a coupler that directs a respective portion of light from the laser beam (not shown) propagating through optical waveguide 120. The respective portions of light are coupled into respective optical resonators 130$a$-$n$ and generate a first or a second resonant wavelength that is detected by the respective detectors 140$a$-$n$. As explained above, the first resonant wavelength is generated when no binding has occurred on a respective binding site 133$a$-$n$, and the second wavelength is generated when a binding is detected at a respective binding site 133$a$-$n$. As can be understood, in this example test procedure, one detector among detectors 140$a$-$n$ indicates a binding event when a single binding has occurred in the array of optical resonators 300. On the other hand, two or more of detectors 140$a$-$n$ indicate that two or more optical resonators 130$a$-$n$ have binding occurrences. Such a configuration permits a concurrent test mode conducted with reference to one specific foreign molecule whereby multiple test results obtained from detectors 140$a$-$n$ can be compared to each other to obtain statistical data of the one specific foreign molecule. The concurrent test mode may also be used to obtain independent diagnostic test results for a variety of foreign molecules. In this variant of the concurrent test mode, each of binding sites 133$a$-$n$ is individually functionalized with a different capture agent that is selected for uniquely binding a corresponding foreign molecule.

In a second example test procedure, each of coupler/switch 115a-n is an optical switch. One of the switches is activated so as to divert all, or a portion, of light from the laser beam propagating through optical waveguide 120. In the example configuration shown in FIG. 2, optical switch 115c is active ("on" state) while all the remaining switches are inactive ("off" state). The light diverted by optical switch 115c is coupled into optical resonator 130c, wherein a first or a second resonant wavelength is generated on the basis of a target molecule being present or absent at binding site 133c. Detector 140c detects the generated first or second resonant wavelength thereby providing an indication of a binding event or absence respectively, inside optical resonator 130c.

In the second example test procedure described above, optical switch 115c may be selectively operated because only the diagnostic test result of optical resonator 130c is desired. In a variant procedure, each of optical switches 115a-n (or a sub-set of optical switches 115a-n) may be sequentially operated to obtain diagnostic test results from multiple optical resonators among optical resonators 130a-n. The sequential operation may conform to a particular pattern or may be carried out in a random pattern and provides for a time-oriented diagnostic test.

Attention is next drawn to the various wavelength-related diagrams shown in FIG. 3. These wavelength-related diagrams illustrate a first example method of operation wherein optical resonators 130a-n are configured for operating at an offset resonant wavelength with respect to a reference wavelength 312 that corresponds to a wavelength of the laser beam propagating through optical waveguide 120. (It may be pertinent to point out that the word "offset" may be referred to herein by alternative words such as "shifted" or "detuned.")

Specifically, wavelength-related diagram 310 shows an offset resonant wavelength 311 that is "blue-shifted" with respect to reference wavelength 312. Offset resonant wavelength 311, as used in this particular method of operation, represents an absence of a binding event at binding site 133a (either because light is not directed through optical resonator 130a, or no binding has occurred even though directed light is present in optical resonator 130a).

In contrast to wavelength-related diagram 310, wavelength-related diagram 320 not only shows an offset wavelength 321 (in dashed line format) but also shows a second wavelength 322. Offset wavelength 321 provides the same indication as offset wavelength 311. However, second wavelength 322 provides an indication that offset wavelength 311 has shifted from the offset wavelength 321 position as a direct result of an occurrence of a binding event inside optical resonator 130c.

The wavelength shifting feature may be implemented in different ways. In a first implementation, the wavelength shift may be designed such that second wavelength 322 coincides with reference wavelength 312. In a second implementation, the change in wavelength may be designed such that second wavelength 322 does not coincide with reference wavelength 312.

Furthermore, depending on the nature of the testing, in one case the extent of the wavelength shift in itself is not necessarily as significant as the fact that a change has occurred thereby signaling that a binding event is currently taking place or has taken place prior to detection. In this case, the wavelength shift may be interpreted as a binary wavelength shift. However, in another case, the wavelength shift is not binary in nature, and a variable amount of the wavelength shift is used as a proportional indicator of the concentration of target molecules (say in a test solution, such as blood).

In a second example method of operation, each of optical resonators 130a-n is configured to have a first resonant wavelength that coincides with reference wavelength 312 when no binding is present. When a binding event takes place in any one or more of optical resonators 130a-n, the first resonant wavelength gets shifted to a second resonant wavelength away from reference wavelength 312. As described above, the shift in wavelength results from one or more foreign molecules binding to a binding site and consequently modifying the refractive index of an optical signal path inside the particular optical resonator. Here again depending on the nature of the testing, in one case the extent of the wavelength shift itself is not necessarily as significant as the fact that a change has occurred thereby signaling that a binding event is currently taking place or has taken place prior to detection. However, in another case, the extent of the wavelength shift is used as a directly proportional indicator of the concentration of target molecules in the tested solution (blood, for example).

In a third example method of operation, each of optical resonators 130a-n is configured to have a first resonant wavelength that coincides with reference wavelength 312 when no binding is present. When a binding event takes place in any one or more of optical resonators 130a-n, the first resonant wavelength gets modified to a point wherein no output signal is available to the corresponding detector. The modification can be carried out in a variety of ways, such as for example, shifting the first resonant wavelength to a wavelength that is not detectable by the corresponding detector, or by causing the optical resonator to stop resonating.

Any of the three example methods of operation described above can be implemented in at least two alternative ways.

In a first implementation, which can be interpreted as constituting a concurrent data collection process, each of coupler/switch 115a-n (whether implemented as a coupler or as an optical switch) is activated so as to divert all, or a portion, of light from optical waveguide 120 to two or more optical resonators 130a-n. The corresponding detectors in detectors 140a-n provide data indicative of the occurrence (or non-occurrence) of a binding event in the two or more optical resonators 130a-n. The data can be retrieved sequentially or concurrently.

In a second implementation, which may be viewed as constituting a polled data collection process, only one of coupler/switch 115a-n (in this embodiment, implemented as an optical switch) is activated so as to divert all, or a portion, of light from optical waveguide 120 to one particular optical resonator amongst optical resonators 130a-n. The corresponding detector provides data indicative of the occurrence or non-occurrence of a binding event in the particular optical resonator. Subsequently, another one of coupler/switch 115a-n is activated and data obtained for another optical resonator. This polling process can then be continued for all or some of the remaining optical resonators.

Either of the two implementations described above can be carried out in various instants in time, for example, to obtain test results over a period of time.

Figure 4:
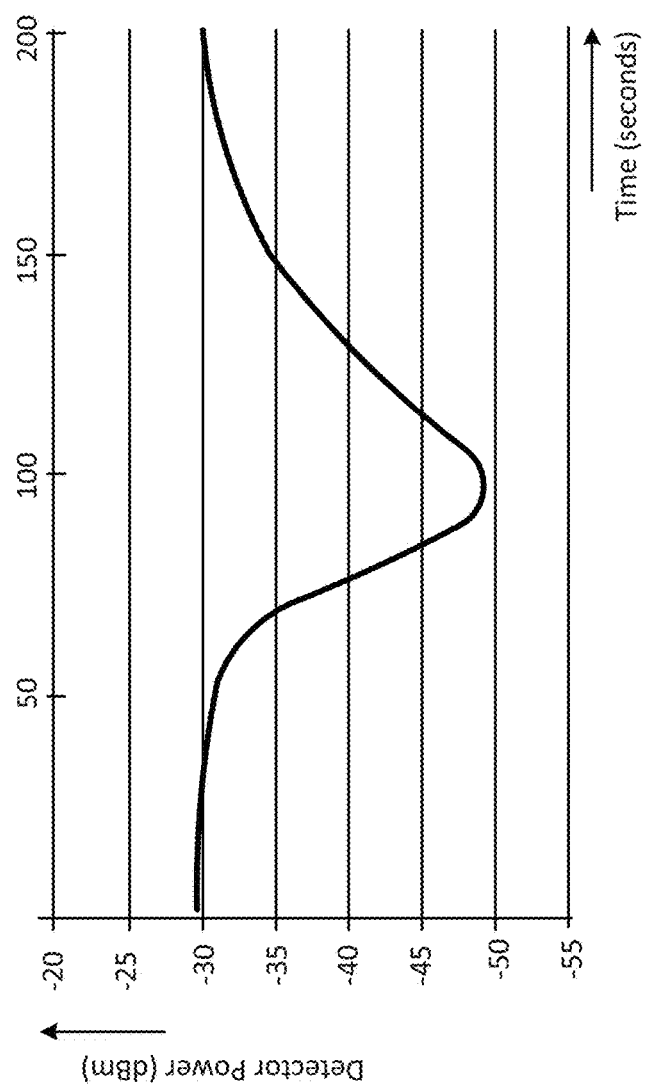
FIG. 4 shows a graph of detector power as a function of time, wherein the detector is part of an implantable diagnostic device in accordance with the present disclosure.

FIG. 4 shows a graph of power generated in a detector (any one of detectors 140a-n) as a result of optical input provided from a corresponding optical resonator (any one of optical resonators 130*a-n*) as a function of time. The change in detected power provides an indication of a binding event.

The structure, fabrication, and prepping of an implantable diagnostic device in accordance with the disclosure will now be described. In a preferred embodiment, the implantable diagnostic device is fabricated as an implantable module containing at least one device that is fabricated using integrated circuit (IC) fabrication techniques incorporating techniques such as lithography and optical/electron beam printing for creating micron-sized circuitry.

For example, each of the optical resonators can be lithographically constructed inside an IC by etching ring or nanobeam resonator patterns through thin silicon membranes supported by silicon dioxide support layers. Additional elements such as the detector, heater, and calorimeter can be fabricated in one or more of the silicon support layers or on additional layers, or can use the geometry of the optical resonator. Metal connections, such as interconnecting tracks, external access pins, ground and power circuits etc., are then provided.

The optical resonators can be functionalized with various capture agents to enable label-free detection of analytes, for example. For detection of coagulants such as thrombin, chemically stable aptamer chemistries have been developed. The optical resonators can be functionalized with these aptamers through a thermally assisted coating process. In such a process, Bis(trimethylsilyl)acetamide (BSA) or Polytetrafluoroethylene (PTFE) is first deposited onto the silicon dioxide surface of the implantable diagnostic device. This deposition process is followed by a local heating process of the optical resonator, during which the BSA is locally removed from the resonator, but remains on the rest of the silicon dioxide surface. Finally, the dioxide surface is coated with the thrombin binding aptamer, which deposits only on the previously heated resonators in which BSA was removed.

DNA immobilization procedures can be implemented by functionalizing the optical resonators using an amino group with a spacer arm (C6) attached to the 5' terminus of the thrombin-binding aptamer (5'-NH2-C6-GGTTGGTGTG-GTTGG-3') and poly (dT)15. A complementary poly (dA)15 could be fluorescently labeled at the 5' terminus using fluorescein phosphoramidite (FAM-poly(dA)15) reporter for laboratory confirmation of an aptamer binding event. The aptamer immobilization will be covalently attachment to a silicon surface of an optical resonator by using a silicon oxide outer layer to which silane reagents can be conjugated. Functionalization of silanoxide optical resonators can be carried out using trialkoxysilane (e.g., trimethoxysilane or triethoxysilane) reagents incorporating aminopropyl such as (3-aminopropyl) triethoxysilane (APTES) in acetone. Specifically, a salinization procedure begins with exposure of a silica surface for ~1-2 hours to a desired silane reagent (APTES) in the vapor phase or in a 5% (v/v) solution of the silane reagent in solvents such as acetone, followed by washing 3 times with acetone and drying in air or under nitrogen. The amino-silanized resonators are then immersed in 1 mM DSS (disuccinimidyl suberate) amino reactive bifunctional covalent cross-linker in DMSO for 1 hour. The substrates are then washed with DMSO and phosphate buffered solution (PBS) (20 mM Na2HPO4, 150 mM NaCl, pH 7.4) for three times and incubated in 500 µL of 60 µM thrombin-binding aptamer in PBS or a mixture of thrombin-binding aptamer containing poly (dT)15 and FAM-poly(dA) 15 in PBS buffer for 2 h. Unreacted thrombin-binding aptamer poly (dT)15 or FAM-poly(dA)15 is removed by washing thoroughly with a buffer solution containing 1% (w/v) BSA and 0.05% Tween-20.

A few non-limiting examples of methods of using an implantable diagnostic device in accordance with the disclosure will now be described.

The first example method pertains to protein detection, and more specifically for detecting protein concentrations in a solution. In this method, an implantable diagnostic device, specifically the optical resonator, is incubated with a target protein at various concentrations in PBS buffer solution at room temperature for 3 hours. After washing with PBS, the resonator is rinsed thoroughly with a buffer and dried for measurement and readout. The binding of the target protein to the binding site results in a shift in wavelength of the optical resonator as described above. The wavelength shift can be directly correlated to the concentration of the target protein in the bulk solution or blood sample. When the detector is subsequently heated, the target protein is released back into the blood sample, and the corresponding reduction in the refractive index change is recorded as a shift in the resonator wavelength. Releasing the target proteins from the binding site prepares the implantable diagnostic device for subsequent use in testing.

Heating raises the temperature of the optical resonator so as to disturb the interactions of the protein binding aptamer with the target protein, thereby providing non-destructive regeneration of the diagnostic device for multiple tests. Significantly, the regeneration can be carried out while the implantable diagnostic device is implanted inside a human body, for example, without removal from inside the human body. Aptamers are known to undergo denaturation/regeneration multiple times without degradation. Another general strategy that can be used to disrupt the aptamer-protein non-covalent interactions is the 2 M NaCl as demonstrated by Baldrich et al. [34] or the use of aqueous solutions of 6 M guanidium chloride which has also been demonstrated by several researchers [35-38]. In case a single regeneration agent is not sufficiently effective, a combination of regeneration reagents can be used.

The second example method pertains to DNA hybridization monitoring. In this method, an implantable diagnostic device, specifically the optical resonator, is functionalized with single stranded target DNA molecules that can serve as hybridization probes. Single-stranded DNA molecules from the sample can then be matched and bonded to this functionalized surface, and the binding of sample to target DNA recorded as a shift in the wavelength of the resonators. The double-stranded DNA resulting from this binding reaction can subsequently be heated and denatured, resulting in a "melting" curve which can be used to confirm the binding energy between the DNA molecules bonded to the binding site. This approach of heating single-stranded molecules in the presence of an enzyme can also lead to DNA amplification at the surface of the resonator, leading to polymerase chain reaction with extremely accurate temperature control. As only the surface of the optical resonators is heated, polymerase chain reaction (PCR) amplification can be selectively performed on that surface within a room-temperature bath. The PCR reaction can also be precisely monitored by using infrared light with little chance of bleaching and no need for fluorescent or other labels. It should be understood that label-free detection of PCR is desirable not only in implanted devices but in-vitro molecular diagnostic tests as well.

The various embodiments of an implantable diagnostic device in accordance with the disclosure can be used to conduct various other types of binding reactions, such as, for example, polymerase chain reaction amplification of hybridized DNA, whereby amplification of a material upon the binding site can be used to obtain higher sensitivity towards, say a nucleic acid target.

Figure 5:
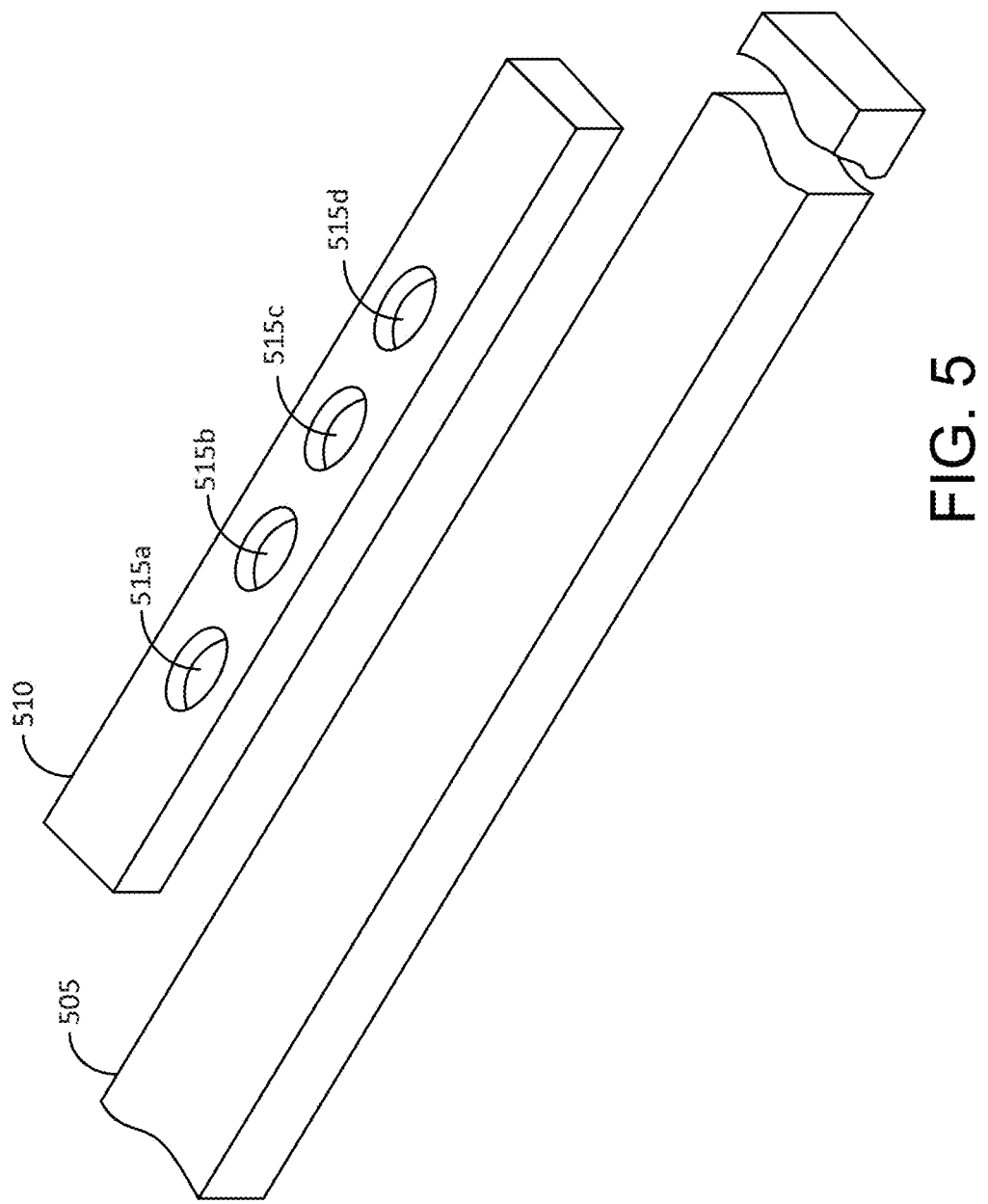
FIG. 5 shows an implantable diagnostic device in accordance with a third embodiment of the present disclosure.

FIG. 5 shows an implantable diagnostic device 500 in accordance with a third embodiment of the present disclosure. In this embodiment, in place of a ring resonator as described above, a linear optical waveguide 510 is configured to contain an array of optical resonators 515a-d. Each of the resonators in the array of optical resonators 515a-d is fabricated by drilling a hole in linear optical waveguide 510. A proximally located pump/probe waveguide 505 cooperates with linear optical waveguide 510 for the assembly to operate as a nanobeam resonator.

Figure 6:
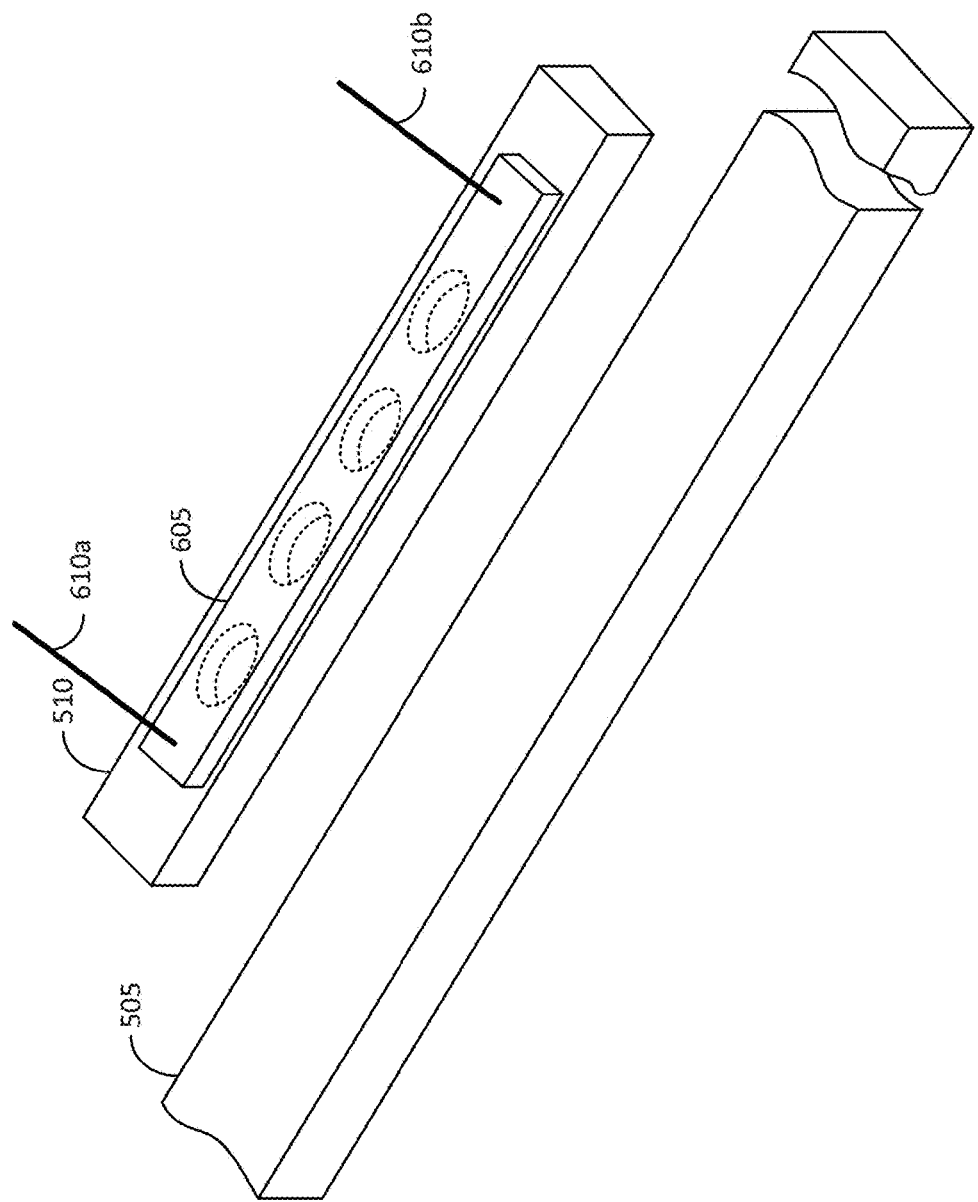
FIG. 6 shows an implantable diagnostic device in accordance with a fourth embodiment of the present disclosure.

FIG. 6 shows an implantable diagnostic device 600 in accordance with a fourth embodiment of the present disclosure. In contrast to the third embodiment, this embodiment includes a heating element 605 that can be implemented as a metal layer mounted upon the array of optical resonators 515a-d. One example material that can be used for the metal layer is Ni—Cr. Contact leads 610a-b are used to provide a suitable electrical stimulus in order to provide heating via heating element 605. In some implementations, the electrical stimulus can be a pulsed stimulus (a pulsed current, for example) that provides controlled heating to specific areas without undesirably heating surrounding tissue or fluids. Furthermore, such a controlled heating allows surrounding tissue and/or fluids to be maintained at their intrinsic quiescent temperature (which may be desirable in certain applications).

In an alternative implementation, heating element 605 is eliminated and contact leads 610a-b are directly connected to some sections (or the entire portion) of linear optical waveguide 510. The silicon material of linear optical waveguide 510 operates as a heating component for heating one or more of the array of optical resonators 515a-d. The combination of this heating component and the predictable refractive index dispersion properties of silicon (shown in FIG. 9) not only enables precise thermo-optic measurements of temperature (for example, within 0.01° C. accuracy), but also enables chemistry analysis of a surface and the use of various types of micro-calorimetric procedures.

In one example application, linear optical waveguide 510 is approximately 0.5 microns wide and 0.2 microns high, whereby optically measured temperature corresponds very closely to a surface temperature at which a binding reaction takes place.

It will be understood that though FIG. 6 indicates an array of optical resonators 515a-d, in certain implementations, a single optical resonator may be used in place of the multiple resonators. Furthermore, though heating element 605 is indicated in FIG. 6 for heating all of the array of optical resonators 515a-d, in alternative implementations, heating element 605 can be configured for localized heating, for example, of one individual optical resonator amongst the array of optical resonators 515a-d, and more specifically for heating only a portion of an optical resonator where the binding site is located.

As indicated above, heating can be used for a number of purposes. Given the low mass of the heated object (for example, an individual optical resonator), heating can be carried out in fast and flexible manner. For example, localized heating provides a good degree of thermal control over a surface of an optical resonator so as to allow local chemistry and functionalization to be carried out only in specific areas wherein detection of resonant optical wavelengths is carried out. Furthermore, occasional heating of an optical resonator helps keep the optical resonator clean by removing unwanted coatings and epithelial cell formations or bio-fouling which often plague implanted refractive index sensors. The cleaning action also enables various other diagnostic test related actions, such as for example, an accurate verification of a bonding energy between one or more adsorbed molecules and one or more capture agents.

Figure 7:
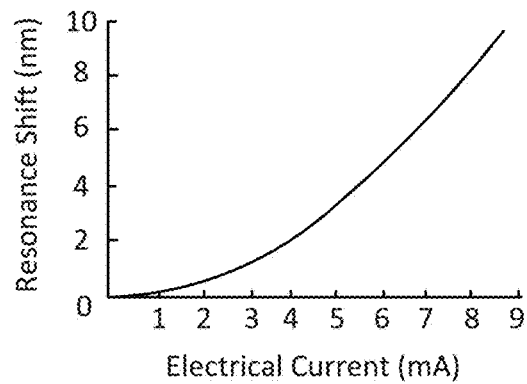
FIGS. 7-9 show graphs characterizing various parameters pertaining to a thermal response of an implantable diagnostic device in accordance with the present disclosure.
Figure 8:
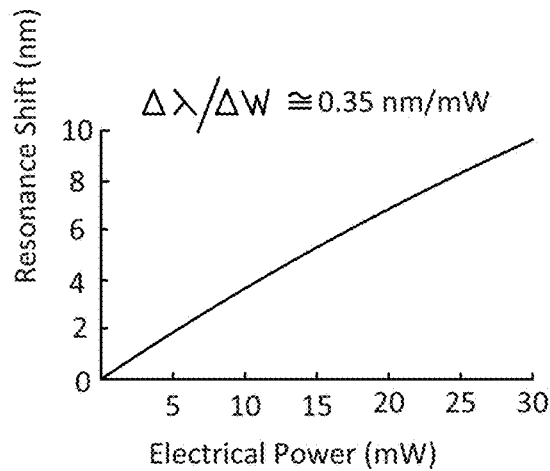
Figure 9:
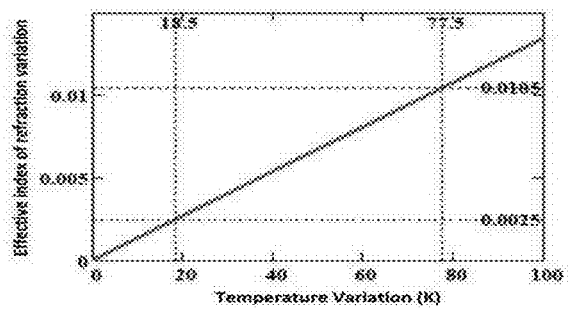

FIGS. 7-9 show graphs characterizing various parameters pertaining to a thermal response of an implantable diagnostic device in accordance with the present disclosure. In one example implementation, the implantable diagnostic device provided a thermo-electric response of 0.35 nm/mW and heating from room temperature to over 100° C. within tens of microseconds.

In conclusion, an implantable diagnostic device in accordance with the present disclosure provides various benefits such as a compact size (thereby allowing implanting of the device inside animate objects); low cost due to incorporation of inexpensive detection circuitry (and the use of conventional IC fabrication techniques); re-usability by heating (thereby allowing multiple diagnostic tests to be performed without removal or discarding of the device); and a configuration that allows performing of simultaneous and/or sequential diagnostic tests for detecting one or more similar or dissimilar target molecules (concurrently or at different times).

The implantable diagnostic devices disclosed herein can be fabricated in silicon-on-insulator material, enabling the use of standard CMOS fabrication technology thereby providing various benefits such as low cost and excellent manufacturability. The manufacturing can include high resolution lithography followed by anisotropic etching of semiconductors. In general, the fabricated implantable diagnostic devices include membranes with perforations (nanobeam resonators as described above using FIGS. 5 and 6) and geometries that incorporate planar photonic crystal cavities. The structure and fabrication provide an ability to design mode geography that ensures efficient overlap between an optical field and an analyte, and also provides for compact devices having reduced mode volume.

The combination of uniform thermal control over surface temperature in the implantable diagnostic devices disclosed herein enables the identification of binding energies through micro-calorimetric measurements related to a binding test, as well as cleaning of the surface to enable quasi-continuous testing for proteins even within complex intravenous chemistry. Thermal control of the optical resonator surface enables precise tuning of the optical resonator to the laser source, thereby leading to simple optical feedback systems and the elimination of additional spectroscopic instrumentation. The features disclosed herein that include enables the manufacture of compact instruments that enable in-vivo continuous monitoring of several metabolites (proteins, DNA strands, or other interesting molecules). The micro-calorimetric measurements enable temperature measurement with an accuracy of approximately 0.01 C as a result of the predictable nature of the refractive index of the material from which the optical resonator is fabricated (for example, silicon). More particularly, a thermo-optic measurement in accordance with the disclosure can be confined to an area of about 100 nm. Some other materials that can be used in lieu of, or in addition to, silicon, include transparent materials with desirable levels of conductivity. A few non-exhaustive list of other materials includes: GaAs, InP, GaN, and/or combinations of InGaAsP, InGaAsN, InGaAlP or InSnO (ITO).

All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The examples set forth above are provided to give those of ordinary skill in the art a complete disclosure and description of how to make and use the various embodiments of the disclosure, and are not intended to limit the scope of what the inventors regard as their disclosure. Modifications of the above-described modes for carrying out the disclosure may be used by persons of skill in the relevant arts, and are intended to be within the scope of the following claims.

A number of embodiments of the disclosure have been described. Nevertheless, it will be understood that various modifications may be made without departing from the spirit and scope of the present disclosure. Accordingly, other embodiments are within the scope of the following claims.

LIST OF REFERENCES

[1] Armani, A. M., Kulkarni, R. P., Fraser, S. E., Flagan, R. C. & Vahala, K. J. Label-Free, Single-Molecule Detection with Optical Microcavities. Science 317, 783 (2007) (published online Jul. 5, 2007 [DOI: 10.1126/science.1145002].).

[2] Horvath, R., Pedersen, H. C., Skivesen, N., Selmeczi, D. & Larsen, N. B. Optical waveguide sensor for on-line monitoring of bacteria. Optics Letters 28, 1233-1235 (2003).

[3] Arnold, S., Khoshsima, M., Teraoka, I., Holler, S. & Vollmer, F. Shift of whispering-gallery modes in microspheres by protein adsorption. Optics Letters 28, 272-274 (2003).

[4] Boyd, R. W. & Heebner, J. E. Sensitive disk resonator photonic biosensor. Applied Optics 40, 5742-5747 (2001).

[5] Vollmer, F. & Arnold, S. Whispering-gallery-mode biosensing: label-free detection down to single molecules. Nature Methods 5, 591-596 (2008).

[6] Ren, H. C., Vollmer, F., Arnold, S. & Libchaber, A. High-Q microsphere biosensor—analysis for adsorption of rodlike bacteria. Optics Express 15, 17410-17423 (2007).

[7] Topolancik, J. & Vollmer, F. All-optical switching in the near infrared with bacteriorhodopsin-coated microcavities. Applied Physics Letters 89,—(2006).

[8] Topolancik, J. & Vollmer, F. Photoinduced transformations in bacteriorhodopsin membrane monitored with optical microcavities. Biophysical Journal 92, 2223-2229 (2007).

[9] Noto, M., Keng, D., Teraoka, I. & Arnold, S. Detection of protein orientation on the silica microsphere surface using transverse electric/transverse magnetic whispering gallery modes. Biophysical Journal 92, 4466-4472 (2007).

[10] Maune B, Lawson R, Gunn C, Scherer A, Dalton, L. "Electrically tunable ring resonators incorporating nematic liquid crystals as cladding layers" APPL PHYS LETT 83 (23): 4689-4691 Dec. 8, 2003.

[11] Baehr-Jones T, Hochberg M, Walker C, Scherer A, "High-Q ring resonators in thin silicon-on-insulator" Applied Physics Letters. 85, no. 16, (2004): 3346.

[12] C. Nylander, B. Leidberg, T. Lind, Gas detection by means of surface plasmon resonance, Sens. Actuators 4 (1982) 299-304.

[13] Yuze Sun and Xudong Fan, "Analysis of ring resonators for chemical vapor sensor development," Opt. Express, 16, 10254-10268 (2008).

[14] W. Lukosz, Principles and sensitivities of integrated optical and surface plasmon sensors for direct affinity sensing and immunosensing, Biosens.Bioelectron. 6 (1991) 215-225.

[15] R. G. Heideman, P. V. Lambeck, Remote opto-chemical sensing with extreme sensitivity: design, fabrication and performance of a pigtailed integrated optical phase-modulated Mach-Zehnder interferometer system, Sens. Actuators B: Chem. 61 (1999) 100-127.

[16] S. Blair, Y. Chen, Resonant-enhanced evanescent-wave fluorescence biosensing with cylindrical optical cavities, Appl. Opt. 40 (2001) 570-582. [5] R. W. Boyd, J. E. Heebner, Sensitive disk resonator biosensor, Appl. Opt. 40 (2001) 5742-5747.

[17] D. J. W. Klunder, et al., Vertically and laterally waveguide-coupled cylindrical microresonators in Si3N4 on SiO2 technology, Appl. Phys. B 73 (2001) 603-608.

[18] E. Krioukov, D. J. W. Klunder, A. Driessen, J. Greve, C. Otto, Sensor based on an integrated optical microcavity, Opt. Lett. 27 (2002) 512-514.

[19] H. Sohlstrom, M. Oberg, Refractive index measurement using integrated ring resonators, in: Proceedings of the 8th European Conference on Integrated Optics ECIO'97, Stockholm, Sweden, 1997, pp. 322-325.

[20] C. Y. Chao, L. J. Guo, Biochemical sensors based on polymer microrings with sharp asymmetrical resonance, Appl. Phys. Lett. 83 (2003) 1527-1529.

[21] Ksendzov, A., Homer, M. L. Manfreda, A. M. "Integrated optics ring-resonator chemical sensor with polymer transduction layer", Electronics Letters 8 Jan. 2004 Vol. 40 No. 1.

[22] A. Ksendzov, Y. Lin, Integrated optics ring-resonator sensors for protein detection, Opt. Lett. 20 (2005) 3344-3346.

[23] F. Vollmer, et al., Protein detection by optical shift of a resonant microcavity, Appl. Phys. Lett. 80 (2002) 4057-4059.

[24] R. W. Boyd, et al., Nanofabrication of optical structures and devices for photonics and biophotonics, J. Mod. Opt. 50 (2003) 2550-3543.

[25] Kwong N, Scherer A, Nanofabrication tools promise new laser manufacturing methods Lightwave October, 2006.

[26] Xiankai Sun, Avi Zadok,* Michael J. Shearn, Kenneth A. Diest, Alireza Ghaffari, Harry A. Atwater, A. Scherer, and Amnon Yariv Electrically pumped hybrid evanescent Si/InGaAsP lasers, May 1, 2009/Vol. 34, No. 9/OPTICS LETTERS.

[27] Baehr-Jones T, Hochberg M, Scherer, A, "Photodetection in silicon beyond the band edge with surface states", OPTICS EXPRESS Volume: 16 Pages: 1659-1668 (2008).

[28] Kihlberg, B. M., Sjobring U., Kastern, U., Bjorck, L. Protein LG: A Hybrid Protein with Unique Immunoglobulin Binding Properties, Journal of Biological Chemistry 267, 25583 (1992).

[29] Kartalov, E.; Zhong, J.; Scherer, A.; Quake, S.; Taylor, C.; Anderson, W. High-Throughput Multi-Antigen Microfluidic Fluorescence Immunoassays. BioTechniques 40: 85-90 (2006).

[30] Kartalov, E. P.; Lin, D. H.; Lee, D. T.; Anderson, W. F.; Taylor, C. R.; Scherer, A. (2008) Internally Calibrated Quantitations of Protein Analyte in Human Serum by Fluorescence Immunoassays in Disposable Elastomeric Microfluidic Devices. Electrophoresis, 29, 5010-5016.

[31] Kartalov, E. P.; Anderson, W. F.; Scherer, A. The Analytical Approach to PDMS Microfluidics and Its Biological Applications. J Nanosci. Nanotech., 6, 2265-2277, (2006).

[32] Ferguson, J. A., Boles, T. C., Adams, C. P., and Walt, D. R. (1996) Nature Biotechnol. 14, 1681-1684.

[33] Myoyong Lee and David R. Walt, A Fiber-Optic Microarray Biosensor Using Aptamers as ReceptorsAnalytical Biochemistry 282, 142-146 (2000).

[34] Baldrich, E., Restrepo, A., O'Sullivan, C. K., Anal. Chem. 2004, 76, 7053-7063.

[35] So, H. M., Won, K., Kim, Y. H., Kim, B. K., Ryu, B. H., Na, P. S., Kim, H., Lee, J. O., Journal of the American Chemical Society 2005, 127, 11906-11907.

[36] Xu, Y., Yang, L., Ye, X., He, P., Fang, Y., Electroanalysis 2006, 18, 1449-1456.

[37] Potyrailo, R. A., Conrad, R. C., Ellington, A. D., Hieftje, G. M., Anal. Chem. 1998, 70, 3419-3425.

[38] Lee, M., Walt, D. R., Analytical Biochemistry 2000, 282, 142-146.

What is claimed is:

1. A diagnostic device fabricated in silicon, the diagnostic device comprising:
    an array of optical resonators, each optical resonator comprising an immunoassay site;
    an optical waveguide configured for coupling coherent light into one or more optical resonators in the array of optical resonators; and
    an array of detectors optically coupled to the array of optical resonators, each detector in the array of detectors configured to detect: a) a first resonant wavelength generated by a corresponding optical resonator, and b) a second resonant wavelength generated by the corresponding optical resonator upon undergoing a change in refractive index by binding of at least one molecule to the immunoassay site,
        wherein each optical resonator is comprised of a substantially circular hole on a surface of the optical waveguide.

2. The diagnostic device of claim 1, wherein each detector generates a first current in response to the first resonant wavelength and a second current in response to the second resonant wavelength.

3. The diagnostic device of claim 2, wherein the first resonant wavelength is selected to substantially coincide with a reference wavelength that is associated with the laser beam propagating through optical waveguide.

4. The diagnostic device of claim 2, wherein the first resonant wavelength is offset with respect to a reference wavelength associated with the laser beam propagating through optical waveguide.

5. The diagnostic device of claim 4, wherein the second current is substantially zero when the corresponding optical resonator undergoes the change in refractive index.

6. The diagnostic device of claim 2, wherein the diagnostic device is packaged in a silicon-based package that is configured for placement inside an animate object.

7. The diagnostic device of claim 6, wherein the silicon-based package comprises a) a silicon substrate, and b) at least one silicon membrane in which the array of optical resonators is fabricated at least in part, by using a lithographic process.

8. The diagnostic device of claim 7, further comprising:
    a capture agent coated on to at least a portion of the at least one silicon membrane to enable label-free diagnostic testing.

9. The diagnostic device of claim 2, further comprising:
    a plurality of heating elements configured for heating a respective one of the array of optical resonators.

10. The diagnostic device of claim 9, wherein the heating is directed at non-destructively regenerating at least one of the immunoassay sites for carrying out additional diagnostic tests.

11. The diagnostic device of claim 9, wherein the heating is directed at obtaining diagnostic data indicative of molecular concentration in a tested fluid.

12. The diagnostic device of claim 11, wherein the tested fluid is a blood sample and the molecular concentration of a target protein in the blood sample.

13. The diagnostic device of claim 1, wherein the optical waveguide is a linear optical waveguide, and the array of optical resonators comprises an array of holes in the linear optical waveguide.

14. The diagnostic device of claim 13, wherein at least a portion of the linear optical waveguide is configured as a heating element for heating one or more of the array of optical resonators.

15. The diagnostic device of claim 1, wherein the optical waveguide is linear and each optical resonator is in a linear array.

16. A diagnostic device fabricated in silicon, the diagnostic device comprising:
    an array of optical resonators, each optical resonator comprising an immunoassay site;
    an optical waveguide configured for coupling coherent light into one or more optical resonators in the array of optical resonators; and
    an array of detectors optically coupled to the array of optical resonators, each detector in the array of detectors configured to detect: a) a first resonant wavelength generated by a corresponding optical resonator, and b) a second resonant wavelength generated by the corresponding optical resonator upon undergoing a change in refractive index by binding of at least one molecule to the immunoassay site,
    wherein each optical resonator is an optical nanobeam resonator made of silicon and the optical waveguide is made of silicon, and wherein each nanobeam optical resonator is comprised of a substantially circular hole on a surface of the optical waveguide.

17. The diagnostic device of claim 16, wherein the optical waveguide is linear and each optical resonator is in a linear array.

18. A diagnostic device fabricated in silicon, the diagnostic device comprising:
- an array of optical nanobeam resonators made of silicon, each optical nanobeam resonator comprising a capture agent located at a binding site;
- an optical waveguide made of silicon, the optical waveguide configured for coupling coherent light into one or more optical nanobeam resonators in the array of optical nanobeam resonators; and
- an array of detectors optically coupled to the array of optical nanobeam resonators, each detector in the array of detectors configured to detect: a) a first resonant wavelength generated by a corresponding optical nanobeam resonator when no binding reaction is present at the corresponding binding site, and b) a second resonant wavelength generated by the corresponding optical nanobeam resonator upon undergoing a change in refractive index when a binding reaction is present at the corresponding binding site,
- wherein each nanobeam optical resonator is comprised of a substantially circular hole on a surface of the optical waveguide.

\* \* \* \* \*